(12) United States Patent
Kawagishi et al.

(10) Patent No.: US 6,352,509 B1
(45) Date of Patent: Mar. 5, 2002

(54) THREE-DIMENSIONAL ULTRASONIC DIAGNOSIS APPARATUS

(75) Inventors: Tetsuya Kawagishi; Naohisa Kamiyama, both of Otawara (JP)

(73) Assignee: Kabushiki Kaisha Toshiba, Kawasaki (JP)

(*) Notice: Subject to any disclaimer, the term of this patent is extended or adjusted under 35 U.S.C. 154(b) by 0 days.

(21) Appl. No.: 09/441,300

(22) Filed: Nov. 16, 1999

(30) Foreign Application Priority Data

Nov. 16, 1998 (JP) .......................... 10-325610

(51) Int. Cl.$^7$ ................................ A61B 8/00
(52) U.S. Cl. ...................... 600/443; 600/447; 600/454; 128/916
(58) Field of Search ................. 600/443, 447, 600/549, 453, 454, 455, 456, 442, 437, 504, 505, 526; 128/916; 367/7, 11; 73/625, 626; 356/28.5

(56) References Cited

U.S. PATENT DOCUMENTS 5,135,000 A * 8/1992 Akselrod et al. .......... 600/458
5,435,310 A * 7/1995 Sheehan et al. ........... 600/443
5,694,945 A * 12/1997 Ben-Haim ................. 600/549
5,860,927 A * 1/1999 Sakaguchi et al. ......... 600/453
5,860,931 A * 1/1999 Chandler .................. 600/458
5,871,019 A * 2/1999 Belohlavek ................ 128/916
5,916,168 A * 6/1999 Pedersen et al. .......... 600/443
6,059,727 A * 5/2000 Foelkes et al. ............ 600/443
6,095,976 A * 8/2000 Nachtomy et al. ......... 600/443

* cited by examiner

Primary Examiner—Marvin M. Lateef
Assistant Examiner—Ali M. Imam
(74) Attorney, Agent, or Firm—Oblon, Spivak, McClelland, Maier & Neustadt, P.C.

(57) ABSTRACT

A three-dimensional ultrasonic diagnosis apparatus has a feature that: transmits ultrasonic beams three-dimensionally to a diagnostic site including a left ventricle of the heart in a subject being examined; receives ultrasonic echo signals thereof; generates three-dimensional data of the diagnostic site based on the received ultrasonic echo signals; determines a cardiac cavity region in generated three-dimensional data; and generates a display image such that information at a myocardial site of the heart is identified by converting a value of the cardiac cavity region in the determined three-dimensional data to a different value. The feature enables the apparatus to provide information on three-dimensional myocardial muscle blood flow useful for clinical diagnosis.

16 Claims, 13 Drawing Sheets

HE: HEART
RA: RIGHT ATRIUM
RV: RIGHT VENTRICLE
LA: LEFT ATRIUM
LV: LEFT VENTRICLE
OB: CARDIAC CAVITY
IS: VENTRICULAR BIPARTITE
MM: MYODARDIAL MUSCLE

M1: ENDOCARDIUM

BL1: BLOOD FLOW IN THE CARDIAC CAVITY
BL2: CORONARY BLOOD FLOW

M: MARKER

BL3: MYOCARDIAL MUSCLE PERFUSION
OB: CARDIAC CAVITY (HIGH BRIGHTNESS)

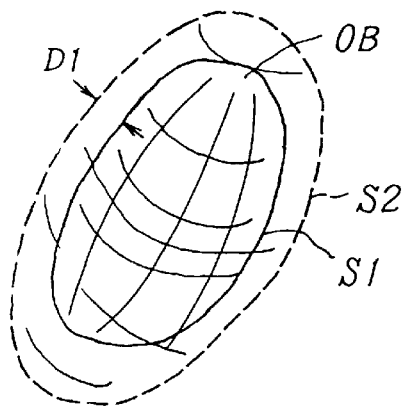
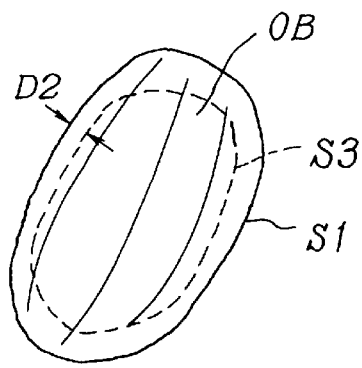
OB: CARDIAC CAVITY
S2: EXTERIOR FACE
OF THE CARDIAC CAVITY
S1: BOUNDARY FACE
OF THE CARDIAC CAVITY
FIG. 7A
OB: CARDIAC CAVITY
S3: INTERIOR FACE
OF THE CARDIAC CAVITY
S1: BOUNDARY FACE
OF THE CARDIAC CAVITY
FIG. 7B
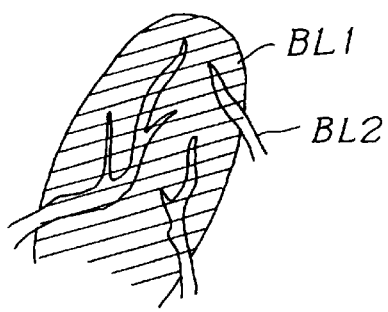
BL1: BLOOD FLOW
IN THE CARDIAC CAVITY
BL2: CORONARY BLOOD FLOW
FIG. 8

BL2a: CORONARY BLOOD FLOW
(FRONT SIDE)
BL2b: CORONARY BLOOD FLOW
(BACK SIDE)

PL: PLANE PASSING THROUGH
LONG AXIS OF THE HEART

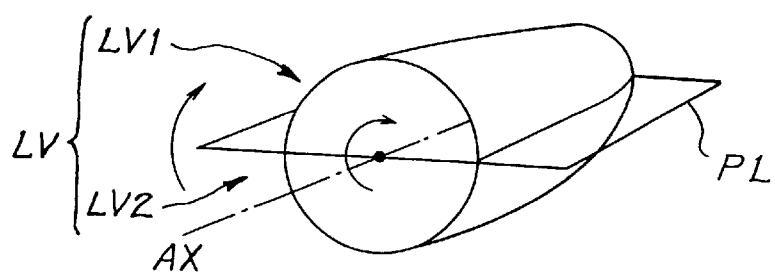
FIG. 18
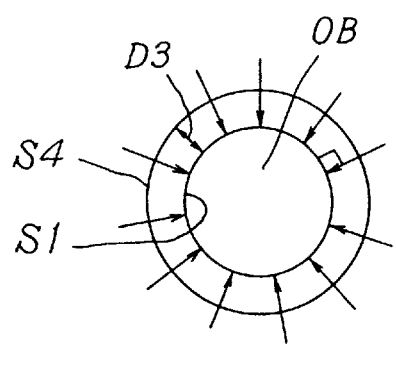
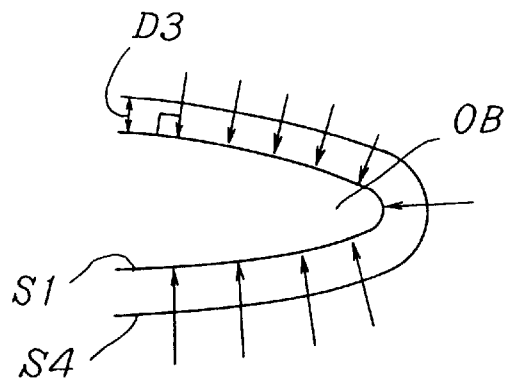
FIG. 19B  FIG. 19A

THREE-DIMENSIONAL ULTRASONIC DIAGNOSIS APPARATUS

BACKGROUND OF THE INVENTION

The present invention relates to a three-dimensional ultrasonic diagnosis apparatus for providing effective information for clinical diagnosis of myocardial ischemia. In particular, the present invention relates to an image processing technique for detecting and displaying a intra-myocardial blood flow from a three-dimensional image.

In clinical diagnosis of the heart, improvement in evaluation techniques of myocardial ischemia is one of the important issues. As an evaluation technology of such myocardial ischemia, conventionally there is known a technique for diagnosing an ischemia site of the heart that is a three-dimensional structure by visualizing coronary arteries of the heart (coronary blood flow) or myocardial perfusion as a two-dimensional ultrasonic image such as a color Doppler image, a power Doppler image, or a contrast image by a Color Doppler method using a ultrasonic diagnosis apparatus or contrast imaging method using a contrast agent.

In the meantime, in recent years, attention is focused on a three-dimensional ultrasonic diagnosis apparatus for scanning ultrasonic beams in a three-dimensional region to construct a three-dimensional image. It is expected to ensure application to clinical diagnosis using a three-dimensional ultrasonic image such as a CFM (Color Flow Mapping) image, a power Doppler image, or a 3D (three-dimensional) contrast image produced by this apparatus.

In view of applying the above mentioned three-dimensional ultrasonic diagnosis apparatus to a clinical diagnosis of the heart, however, in a three-dimensional image when the heart targeted for diagnosis is scanned three-dimensionally, blood flow in the cardiac cavity, coronary blood flow, and myocardial perfusion are displayed in a superimposed manner each other. Thus, there is a problem that these blood flow and perfusion are hardly discriminated, thus making it difficult to diagnose myocardial ischemia three-dimensionally. This problem cannot be found in the case of a conventional ultrasonic diagnosis apparatus for displaying a two-dimensional image.

SUMMARY OF THE INVENTION

The present invention has been achieved in view of such a conventional problem. It is an object of the present invention to provide information on a three-dimensional myocardial blood flow useful for clinical diagnosis by clearly displaying information on coronary blood flow of the heart or perfusion discriminated from the blood flow in the cardiac cavity even if a three-dimensional ultrasonic image is utilized.

In order to achieve the foregoing object, the inventor focused attention to adopt means for masking a blood flow image in the cardiac cavity, for example, 1) means for automatically extracting a cardiac endocardium from a ultrasonic monochrome image, thereby to mask an inside thereof; 2) means for automatically extracting the blood flow in the cardiac cavity from a Color Doppler or Power Doppler image to mask it; 3) means for automatically extracting the blood flow in the cardiac cavity from a contrast image based on a contrast imaging method using a contrast agent, thereby to mast it; and means for displaying a coronary blood flow or perfusion in the myocardium by means of MIP (Maximum or Minimum Intensity Projections), Integral Value Projection, volume rendering or the like after it has been masked by these masking means.

A three-dimensional ultrasonic diagnosis apparatus according to the present invention has been completed based on such attention.

That is, according to a first aspect of the invention, there is provided a three-dimensional ultrasonic diagnosis apparatus comprising: means for transmitting ultrasonic beams three-dimensionally to a diagnostic site including a left ventricle of the heart in a subject being examined and for receiving means for receiving ultrasonic echo signals thereof; three-dimensional data generating means for generating three-dimensional data of the diagnostic site based on the ultrasonic echo signals received by the receiving means; cardiac cavity region determining means for determining a cardiac cavity region in three-dimensional data generated by the three-dimensional data generating means; and display image generating means for generating a display image such that information at a myocardial site of the heart is identified by converting a value of the cardiac cavity region in the three-dimensional data determined by the determining means to a different value.

According to a second aspect of the invention, there is provided the apparatus according to the first, wherein the three-dimensional data generating means generates at least one of morphological information and blood flow information of the diagnostic site.

According to a third aspect of the invention, there is provided the apparatus according to the second aspect, wherein the cardiac cavity region determining means is adopted to extract a cardiac endocardium from morphological information of the diagnostic site generated by the three-dimensional data generating means, and obtain a cardiac cavity region based thereon.

According to a fourth aspect of the invention, there is provided the apparatus according to the second aspect, wherein the cardiac cavity region determining means is adopted to obtain a cardiac cavity region based on blood flow information on the diagnostic site generated by the three-dimensional data generating means.

According to a fifth aspect of the invention, there is provided the apparatus according to the third or the fourth aspect, wherein the cardiac cavity region determining means is adopted to obtain a cardiac cavity region based on three-dimensional data obtained based on ultrasonic echoes obtained in a state in which a contrast agent is injected into the subject.

According to a sixth aspect of the invention, there is provided the apparatus according to the first and fifth aspects, wherein the display image generating means is adopted to generate a display image based on data excluding the data in the cardiac cavity region in the three-dimensional data.

According to a seventh aspect of the invention, there is provided the apparatus according to the sixth aspect, wherein the display image is a two-dimensional image obtained by projection of the three-dimensional data.

According to a eighth aspect of the invention as claimed in claim 8, there is provided the apparatus according to seventh aspect, wherein the two-dimensional image is obtained by using a predetermined projection method to project brightness information on data included in a region between a boundary face of the cardiac cavity in the three-dimensional data and a reference curved surface set from the boundary face with an arbitrary distance from the reference curved surface side.

According to a ninth aspect of the invention, there is provided the apparatus according to eighth aspect, wherein the projection method has an MIP (Maximum or Minimum Intensity Projection) method.

According to a tenth aspect of the invention, there is provided the apparatus according to the eighth aspect, wherein the projection method has an integral value projection method.

According to an eleventh aspect of the invention, there is provided the apparatus according to the seventh aspect, wherein the two-dimensional image is a partial image of the three-dimensional data.

According to a twelfth aspect of the invention, there is provided the apparatus according to the eleventh aspect, wherein the partial image is included in a partial region in which the left ventricle of the heart is divided by a plane including a longer axis thereof.

According to a thirteenth aspect of the invention, there is provided the apparatus according to the twelfth aspect, wherein the apparatus further comprising means for detecting a long axis of the left ventricle of the heart based on a cardiac cavity determined by the cardiac cavity region determining means.

According to a fourteenth aspect of the invention, there is provided the apparatus according to a thirteenth aspect, wherein the means for determining the long axis of the left ventricle of the heart is means for detecting one of a plurality of inertial main axes defined by morphology of the cardiac cavity as a long axis of the left ventricle of the heart.

According to a fifteenth aspect of the invention, there is provided a three-dimensional ultrasonic diagnosis apparatus comprising: means for transmitting ultrasonic beams three-dimensionally to a diagnostic site including a left ventricle of the heart in a subject being examined and for receiving ultrasonic echo signals thereof; means for generating three-dimensional blood flow information data of the diagnostic site based on the ultrasonic echo signals received by the transmitting and receiving means; means for determining a cardiac cavity region in the blood flow information data generated by the generating means; and means for generating a display image in which blood flow information on the cardiac cavity region determined by the determining means is eliminated.

According to a sixteenth aspect of the invention, there is provided a three-dimensional ultrasonic diagnosis apparatus comprising: means for transmitting ultrasonic beams three-dimensionally to a diagnostic site including a left ventricle of the heart in a subject being examined and for receiving ultrasonic echo signals thereof; three-dimensional data generating means for generating three-dimensional blood flow information based on the ultrasonic echo signals received by the receiving means; display image generating means for generating a display image so that a region with less blood flow in a myocardial muscle of the heart is identified by differentiating an image processing method depending on a myocardial region and a cardiac cavity region of the heart based on the three-dimensional blood flow information generated by the three-dimensional data generating means; and means for displaying the display image generated by the display image generating means.

As has been described above, in a three-dimensional ultrasonic diagnosis apparatus according to the present invention, a local myocardial muscle blood flow of the entire left ventricles of the heart can be simply evaluated objectively and quantitatively, and information useful for clinical diagnosis can be provided.

BRIEF DESCRIPTION OF THE DRAWINGS

The accompanying drawing which are incorporated in and constitute a part of this specification, illustrate embodiments of the present invention and, together with the description, serve to explain the principles of the present invention; in which:

FIGS. 7A and 7B are schematic views illustrating an example of setting a detected cardiac cavity;

FIG. 8 is schematic view illustrating an MIP display example of three-dimensional blood flow information (Color Doppler) when the inside of a cardiac cavity is not masked;

FIGS. 11A and 11B are conceptual views each illustrating a display example of a divided image of the left ventricle, wherein FIG. 11A is a view showing an image when a narrow is absent; and FIG. 11B is a view showing an image when a narrow is present;

FIGS. 15A and 15B are conceptual views showing a display example of a divided image of the left ventricle displayed as a contrast image, wherein FIG. 15A is a view showing an image when a ishemia is absent; and FIG. 15B is a view showing an image when the ishemia is present.;

FIG. 18 is a conceptual view illustrating an example when a division plane of the left ventricle is rotated;

FIGS. 19A and 19B are conceptual views each illustrating MIP on the cardiac cavity boundary face;

DESCRIPTION OF THE PREFERRED EMBODIMENTS

Hereinafter, preferred embodiments of a three-dimensional ultrasonic diagnosis apparatus according to the present invention will be described with reference to the accompanying drawings.

Figure 1:
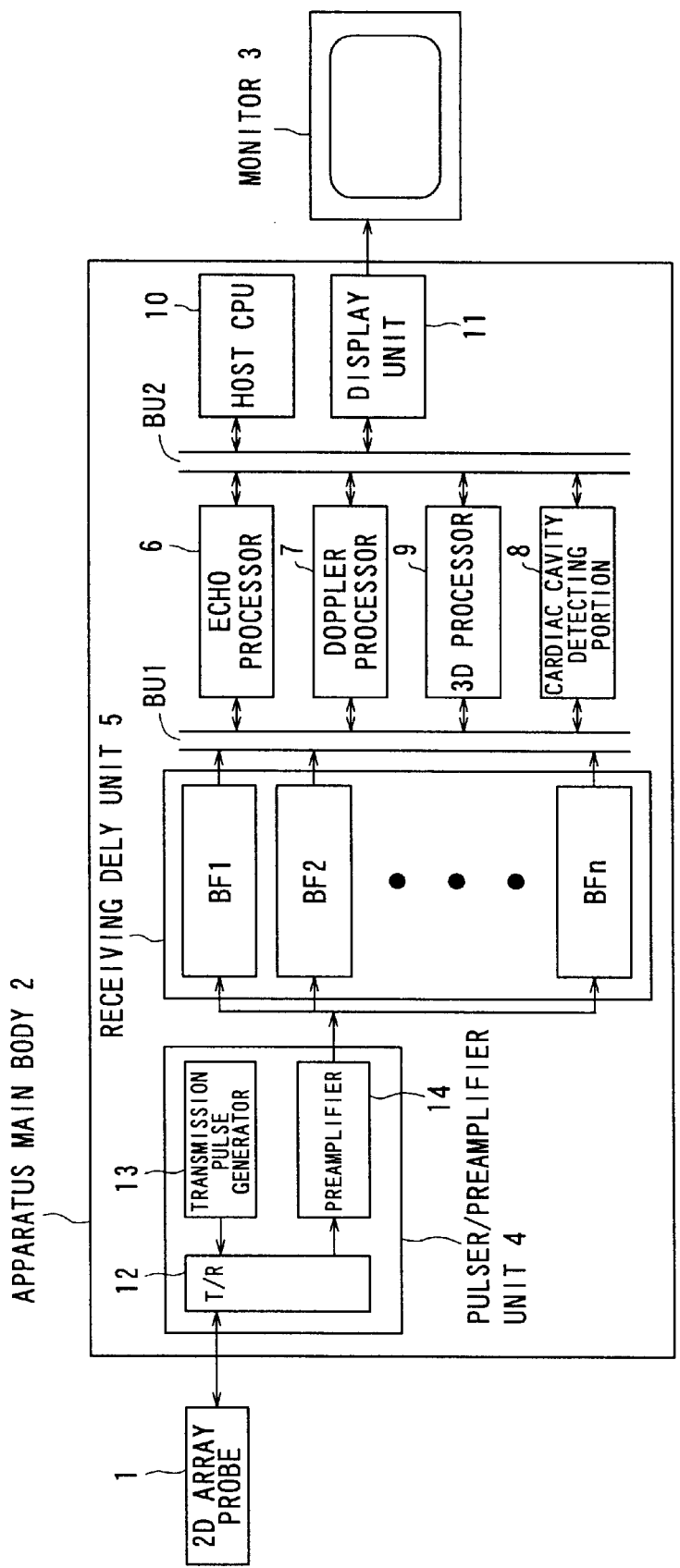
FIG. 1 is a schematic block diagram showing one embodiment of the three-dimensional ultrasonic diagnosis apparatus according to the present invention.

A ultrasonic diagnosis apparatus shown in FIG. 1 is applied as a real-time three-dimensional system for acquiring a ultrasonic three-dimensional image that can be used for clinical diagnosis of myocardial ischemia, for example, in real-time. That is, this ultrasonic diagnosis apparatus comprises a two-dimensional array probe 1 having a plurality of piezoelectric transducers arrayed in two-dimensional array shape; an apparatus main body 2 to be connected to this probe 1; and a monitor 3 to be connected to this main body 2.

The two-dimensional array probe 1 causes a plurality of piezoelectric transducers to be driven under the control of the apparatus main body 2. In this manner, ultrasonic beams emitted by each of the transducers of the probe 1 are scanned three-dimensionally toward a diagnostic site in a subject to be examined along transmission beam forming conditions in which ultrasonic beams are predetermined. For these ultrasonic beams, ultrasonic echo signals reflected on an acoustic impedance boundary in internal tissues of the subject or backward-scattered by a fine scattering element are converted to echo signals each having a finely weak voltage quantity, and are received. The received signals are transmitted to the apparatus main body 2.

The apparatus main body 2 comprises a pulser/preamplifier unit 4 to be connected to the probe 1; a receiving delay circuit 5 to be connected to a preamplifier output side of this unit 4; a plurality of processors, i.e., an echo processor 6, a Doppler processor 7, a cardiac cavity detecting portion 8, and 3D processor 9 to be connected to this receiving delay circuit 5 via a first bus BU1; and a host CPU 10 and a display unit 11 to be connected to each of these processors via a second bus BU2.

The pulser/preamplifier unit 4 comprises a transmission pulse generator 13 for generating a pulse voltage for controlling the direction and convergence of ultrasonic beams using the probe 1; a T/R 12 for supplying a driving signal to the probe 1 based on a pulse voltage from this generator 13; and a preamplifier 14 for receiving a receive signal of the probe 1.

The receiving delay circuit 5 comprises a plurality (n-pieces) of circuit sets for controlling the direction and convergence of ultrasonic beams based on predetermined three-dimensional reception beam forming conditions and for performing parallel, simultaneous reception of a plurality of ultrasonic beams. i.e., BF (Beam Former) 1 to BFn.

The echo processor 6 detects orthogonal wave signals for received signals from the receiving delay circuit 5 based on a predetermined reference frequency; generates three-dimensional spatial distribution image data indicative of three-directional morphological information (contrast image including information on the contrast agent when it is used) in the subject according to the signal amplitude of the detected orthogonal wave signals; and feeds this generated three-dimensional spatial distribution image data to the cardiac cavity detecting portion 8.

The Doppler processor 7 measures time variation of a phase of the received signals from the receiving delay circuit 5, thereby to generate three-dimensional spatial distribution image data on at least one of velocity, power, and dispersion indicative of blood flow information of the subject's heart and its periphery and transmit this three-dimensional spatial distribution image data to the cardiac cavity detecting portion 8.

The cardiac cavity detecting portion 8 comprises processors for executing a predetermined cardiac cavity detection algorithm, for example, and detects data concerning the cardiac cavity of the left ventricle of the heart based on three-dimensional spatial distribution data from the echo processor 6 or Doppler processor 7 by way of these processors.

Here, a concept of an algorithm that this cardiac cavity detecting portion 8 executes will be described in the case where: 1) three-dimensional morphological information from the echo processor 6 is employed; 2) three-dimensional blood flow information from the Doppler processor 7 is employed; and 3) a contrast image is employed based on a contract imaging method using a contrast agent.

First, in the case of 1), i.e., in the case where three-dimensional morphological information is employed, there are used a boundary detecting method utilizing a difference in image data brightness, for example, a method for performing image binary coding or pixel value differentiation or improving a algorithm such as ACT practically used for a two-dimensional image for the purpose of a three-dimensional image.

Figure 2:
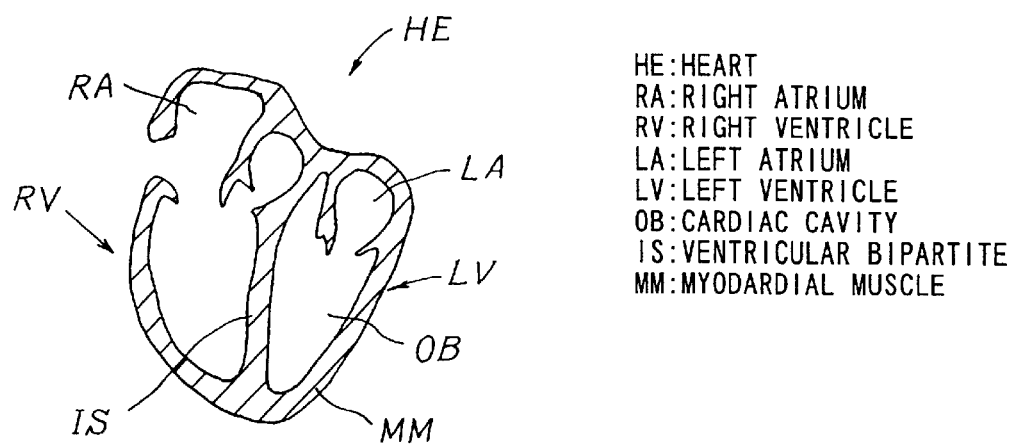
FIG. 2 is a schematic view showing the entire heart as a diagnostic site.
Figure 3:
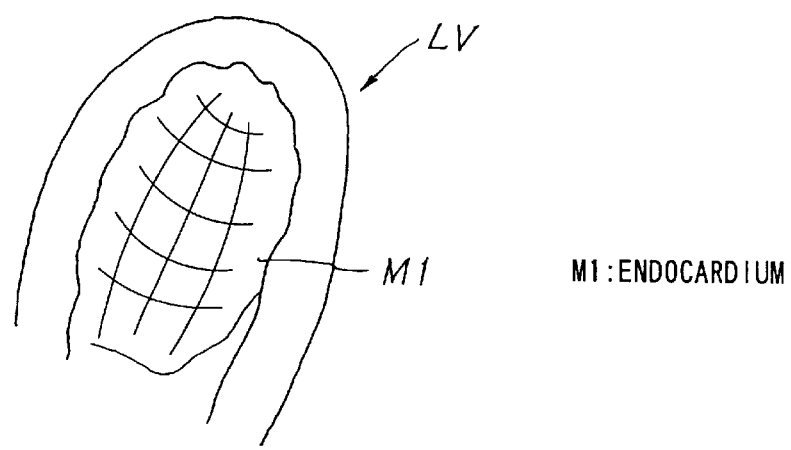
FIG. 3 is a schematic view showing a left ventricle of the heart.

Then, as shown in FIGS. 2 and 3, data of a cardiac endocardium (tunica intima) M1 of a left ventricle LV corresponding to the boundary position of a cardiac cavity OB of the left ventricle LV is extracted from three-dimensional morphological information whose range includes a left ventricle LV in a heart HE by the above-mentioned boundary detecting method, and such extracted data of the endocardium M1 is set.

This endocardium M1 can be manually extracted while an operator is looking at a screen on the monitor 3. Alternatively, in the case where a cardiac tunica externa of the left ventricle LV (the boundary position on a right ventricle RV side of the heart HE is included in a ventricular bipartite (interventricular septum) IS in FIG. 2) is extracted more easily than the endocardium M1 thereof, it is possible to set a position spaced from the extracted cardiac tunica externa with a certain distance as a virtual endocardium M1. Thus, based on the endocardium M1 (cardiac cavity boundary face) automatically or manually extracted and set from three-dimensional morphological information, the internal part of the endocardium M1 is detected as cardiac cavity data. In this case, detection can be implemented without using a contrast agent in particular.

Figure 4:
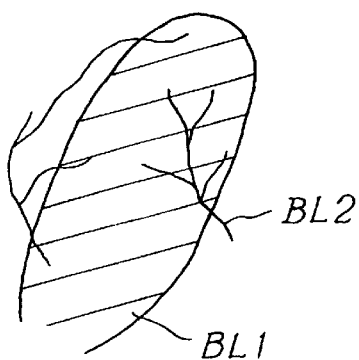
FIG. 4 is a schematic view illustrating a superimposed display of blood flow information when the inside of a cardiac cavity is not masked.
Figure 5:
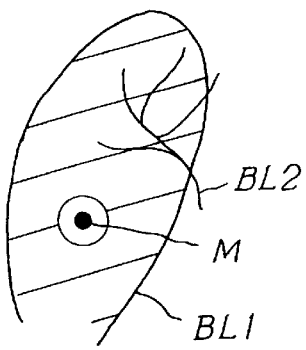
FIG. 5 is a schematic view illustrating a case when a cardiac cavity is set utilizing a marker.

In the case of 2), i.e., in the case where three-dimensional blood flow information is employed, an algorithm utilizing a brightness difference similar to that shown in the above 1) is applied to a Doppler signal (image), thereby to automatically extract a boundary face between a cardiac cavity blood flow BL1 and a coronary blood flow BL2 in the left ventricle LV shown in FIG. 4 and to detect its internal position as cardiac cavity data. In this case, the boundary face can be manually set while the operator is looking at the screen in the same way as the above. In addition, as shown in FIG. 5, a part of the cardiac cavity blood flow BL1 is specified by utilizing a marker M displayed in the screen, thereby making it possible to set all the blood flow site associated therewith in the cardiac cavity OB. In this case, the coronary blood flow BL2 can be separated because it does not come into contact with the cardiac cavity blood flow BL1, three-dimensionally.

Figure 6:
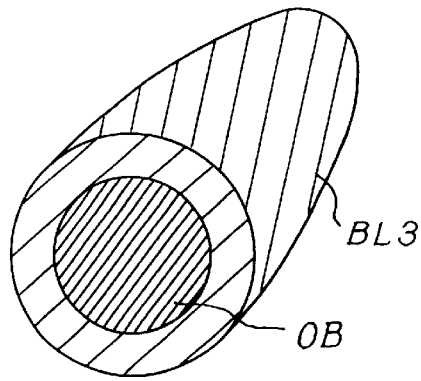
FIG. 6 is a schematic view illustrating a brightness difference of blood flow information in a contrast image.

In the case of 3), i.e., in the case where a contrast image is employed, as shown in FIG. 6, when a contrast agent consisting essentially of micro bubbles to be injected from a vein, for example, is used, the echo of the blood blow BL2 in the cardiac cavity is enhanced brighter than the echo of perfusion BL3 (including the coronary blood flow BL2) around it. Thus, the cardiac cavity boundary is extracted utilizing the brightness difference between these, and its inside is detected as cardiac cavity OB. This effect becomes more significant by adopting a contrast image obtained by harmonic imaging (HM).

The data on cardiac cavity OB detected in any of the above 1) to 3) can be slightly smaller or larger than it really is. For example, the cardiac cavity data detected from the morphological information stated in the above 1) is expected to be smaller than it really is by the influence of a trabeculae carneae in the heart, and the cardiac cavity OB detected from the blood flow information stated in the above 2) or a contrast image stated in the above 3) is expected to be larger than it really is by the influence of low-resolving power.

To overcome this problem, in the case where the cardiac cavity is expected to be smaller than it really is, as shown in FIG. 7A, a cardiac cavity exterior face S2 spaced with an arbitrary distance D1 is set as a cardiac cavity OB outwardly from the boundary face S1 of the cardiac cavity OB. In addition, in the case where the cardiac cavity OB is expected to be larger than it really is, as shown in FIG. 7B, a cardiac cavity interior face S3 spaced with an arbitrary distance D2 inwardly from the boundary face S1 of the cardiac cavity OB.

The 3D processor 9 is adopted to mask image data of the cardiac cavity OB detected by the cardiac cavity detecting portion 8 from three-dimensional spatial distribution image data from the echo processor 6 and Doppler processor 7, and display its blood flow image on the monitor 11 via the display unit 11. As a method for displaying this blood flow image, any of MIP, integral value projection, surface rendering, and volume rendering or the like may be employed.

Hereinafter, a concept of mask processing using this 3D processor 9 will be described by referring to FIG. 8 to FIG. 16.

Now, a case in which an image is displayed without masking the cardiac cavity OB will be described. FIG. 8 shows an example when three-dimensional blood flow information acquired by three-dimensional CFM is MIP-displayed. In this case, the blood flow in the cardiac cavity BL1 and the coronary blood flow BL2 are displayed in a superimposed manner, thus making it difficult to identify the coronary blood flow BL2 and making it impossible to diagnose myocardial ischemia.

Figure 9:
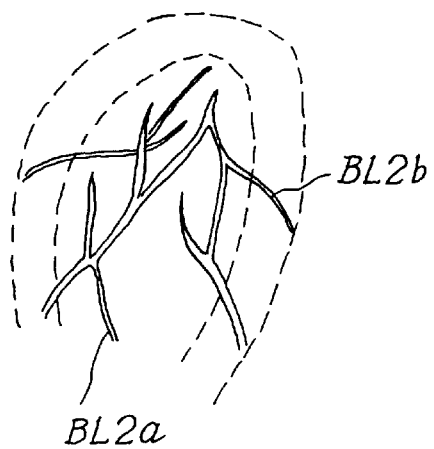
FIG. 9 is a schematic view illustrating a superimposed display between the front side and the back side of a coronary blood flow after myocardial muscle masking.

The thus detected myocardial cavity OB is masked from three-dimensional blood flow information, and an MIP display image is obtained, thereby visualizing only the coronary blood flow BL2 as shown in FIG. 9. However, this coronary blood flow BL2 includes information on the entire myocardial muscle of the left ventricle. In this state, the front-side coronary blood flow BL2a and the back-side coronary blood flow BL2b are displayed in a superimposed manner, thus making it difficult to diagnose myocardial ischemia.

Figure 10:
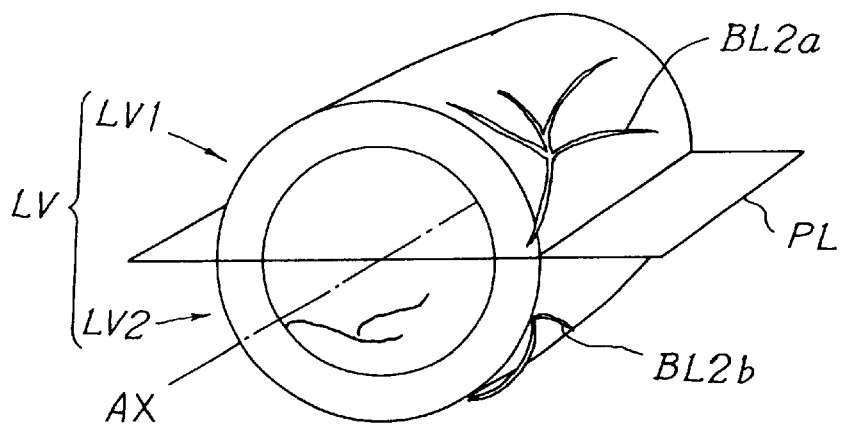
FIG. 10 is a conceptual view illustrating a division example of the left ventricle.
Figure 11A:
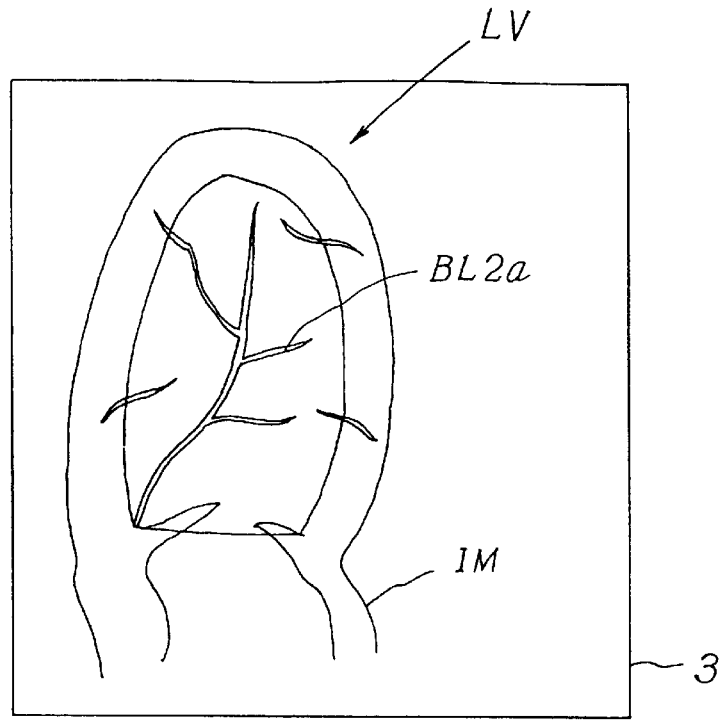
Figure 11B:
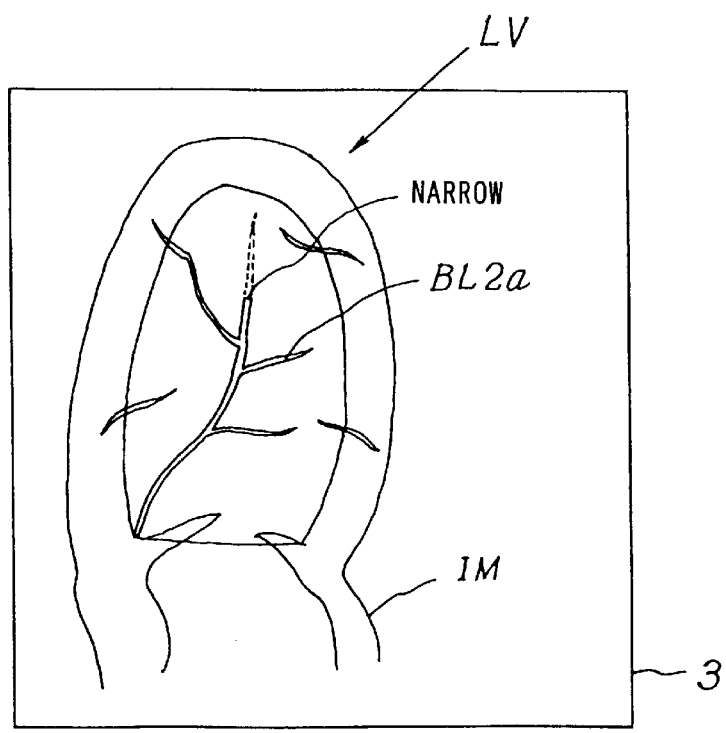

To overcome this difficulty, as shown in FIG. 10, the left ventricle LV of the heart is divided into two sections; front-side left ventricle LV1 and back-side left ventricle LV2 on a division plane PL passing through its long axis AX. For example, the front-side left ventricle LV1 is MIPed (maximum intensity projected), and the back-side left ventricle LV2 is masked, thereby making it possible to display only the front-side left ventricle, i.e., only front-side coronary blood flow BL2a on the monitor 3 as shown in FIG. 11. At this time, morphological image IM of the left ventricle LV on the division plane PL (normal two-dimensional ultrasonic image representing morphology of the heart) may be displayed by superimposing the MIP image divided into two sections as shown in FIG. 11A and FIG. 11B, thereby making it possible to clarify a positional relation with blood vessels. FIG. 11A shows an image when a narrow is absent; and FIG. 11B shows an image when a narrow is present, respectively. As shown in FIG. 11B, when a narrow is present, an image is displayed as if it were drilled, making it possible to easily identity the narrow.

Although the above mentioned mask processing shows an example of using three-dimensional blood flow information, the processing is executed similarly for a perfusion imaging or coronary blood flow imaging based on the contrast image. This fact is shown in FIG. 12 to FIG. 15.

Figure 12:
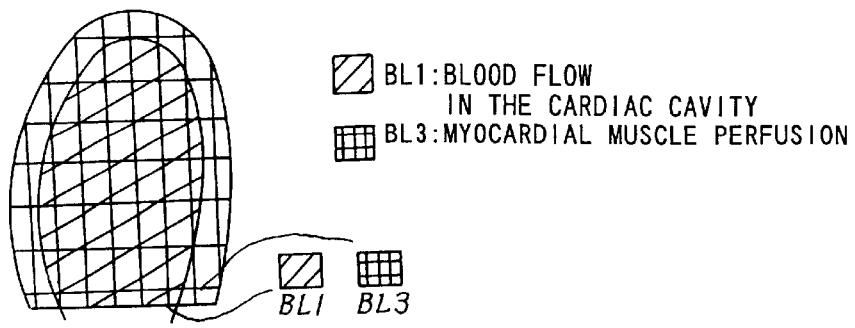
FIG. 12 is a schematic view illustrating a display example of a contrast image when the inside of a cardiac cavity is not masked.

That is, in the case where an image is displayed without masking the cardiac cavity OB, when a three-dimensional image of myocardial muscle perfusion is displayed using a contrast imaging method, the echoes of the blood flow in the cardiac cavity BL1 and myocardial muscle perfusion BL3 are superimposed with each other, making it possible to identify both of these echoes, as shown in FIG. 12.

Figure 13:
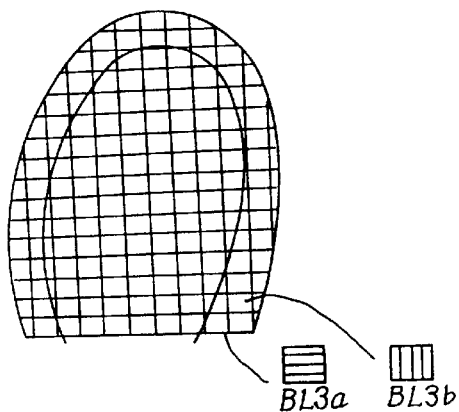
FIG. 13 is a schematic view illustrating a superimposed display between the front side and the back side of a coronary blood flow after myocardial muscle masking has been done for a contrast image.

As shown in FIG. 13, the echoes of the blood flow in the cardiac cavity BL1 are masked, thereby making it Possible to visualize only perfusion BL3. However, this perfusion BL3 includes information on the entire myocardial muscle of the left ventricle. In this state, the front-side perfusion BL3a and the back-side perfusion BL3b are superimposed with each other, making it possible to diagnose myocardial ischemia.

Figure 14:
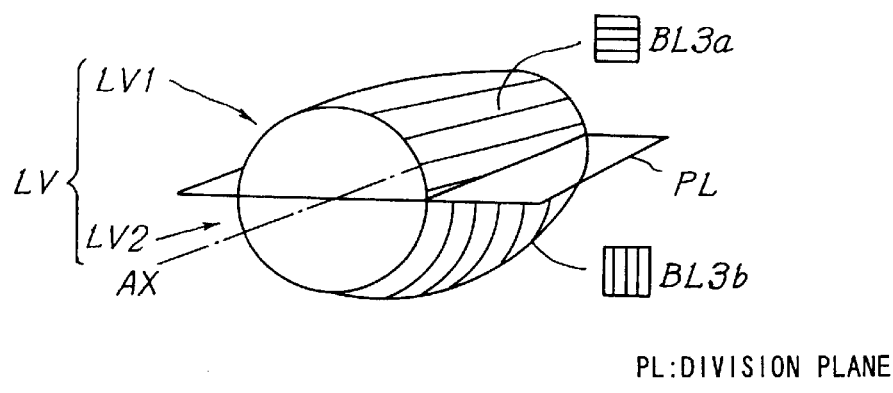
FIG. 14 is a conceptual view illustrating a division example of the left ventricle displayed as a contrast image.
Figure 15A:
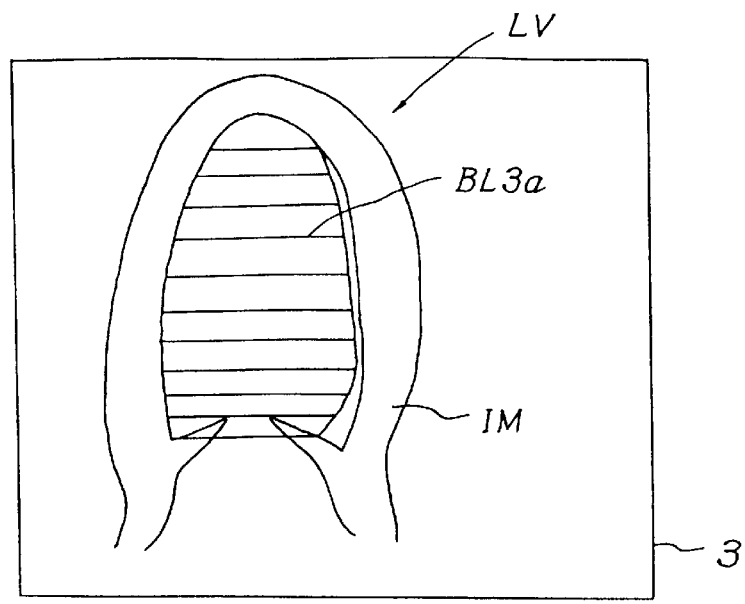
Figure 15B:
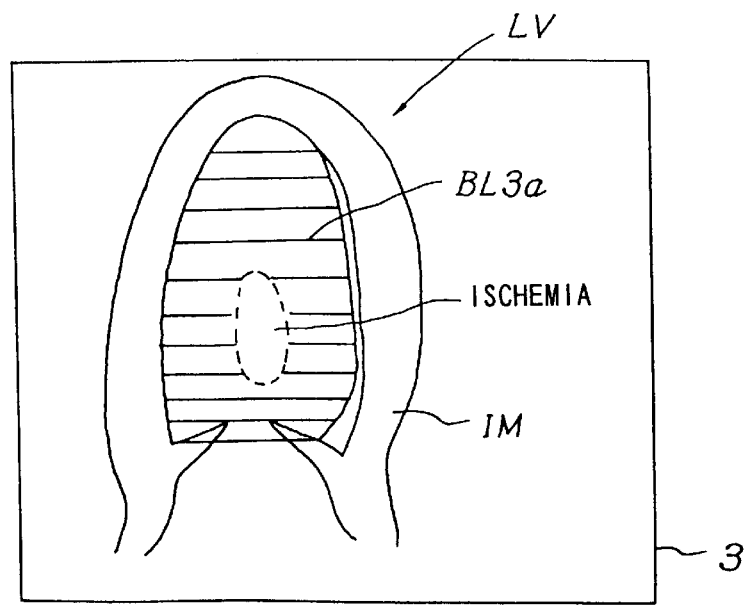

As shown in FIG. 14, the left ventricle LV of the heart is divided into two sections, i.e., front-side left ventricle LV1 and back-side left ventricle LV2 on the division plane PL passing through its long axis AX. For example, the front-side left ventricle LV1 is MIPed (Maximum Intensity Projected), and the back-side left ventricle is masked, thereby making it possible to display only the front-side left ventricle LV1, i.e., only front-side perfusion BL3a on the monitor 3 as shown in FIGS. 15A and 15B. At this time, morphological image IM of the left ventricle LV on the division plane PL (normal two-dimensional ultrasonic image representing morphology of the heart) may be displayed by superimposing a perfusion image divided into two sections as shown in FIG. 15A and FIG. 15B, thereby making it possible to clarify a positional relation with blood vessels. FIG. 15A shows an image when a ishemia (or week enhance by a narrow) is absent; and FIG. 15B shows an image when the ishemia is present, respectively. As shown in FIG. 15B, when the ishemia is present, an image is displayed as if it were drilled, making it possible to easily identify the ishemia.

Therefore, according to the illustrative embodiment, even in the case of a three-dimensional image, local cardiac functions of the entire left ventricle of the heart can be simply evaluated objectively and quantitatively, and information useful for clinical diagnosis can be provided.

In the above mentioned illustrative embodiment, a 2D array probe 1 and a Pulser/preamplifier unit 4 comprises transmitting and receiving means; a receiving delay circuit 5, an echo processor 6, and a Doppler processor 7 comprises three-dimensional data generating means; a cardiac cavity detecting portion 8 comprises cardiac cavity region determining means; and a 3D processor 9, a display unit 11, and a monitor 3 comprises display image generating means, respectively. Of course, the present invention is not limited thereto, and can be altered and practiced without departing from spirits thereof.

That is, display image generating means may be adopted to generate any one or combined images of: 1) a display image in which information at a myocardial muscle site of the heart can be easily identified by converting a value in the cardiac cavity region into a different value in three-dimensional data; 2) a display image in which blood flow information in the cardiac cavity region is subtracted; and 3) a display image in which a region with less blood flow in myocardial muscles can be easily identified by differentiating an image processing method depending on the myocardial muscle and cardiac cavity regions of the heart.

Figure 16:
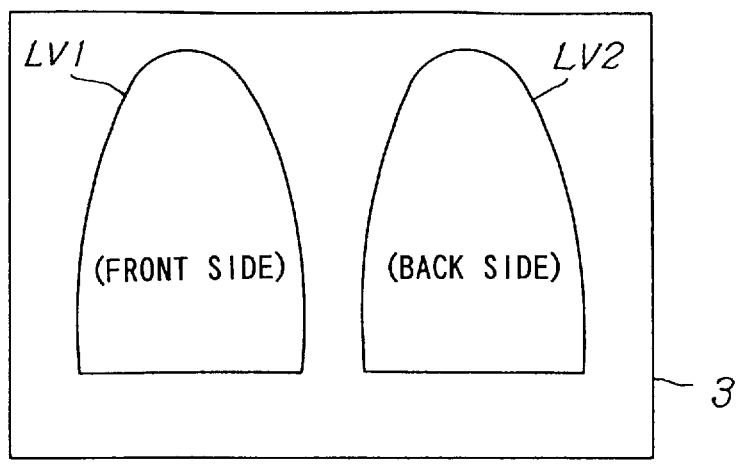
FIG. 16 is a conceptual view showing a parallel display example of a divided image of the left ventricle.
Figure 17:
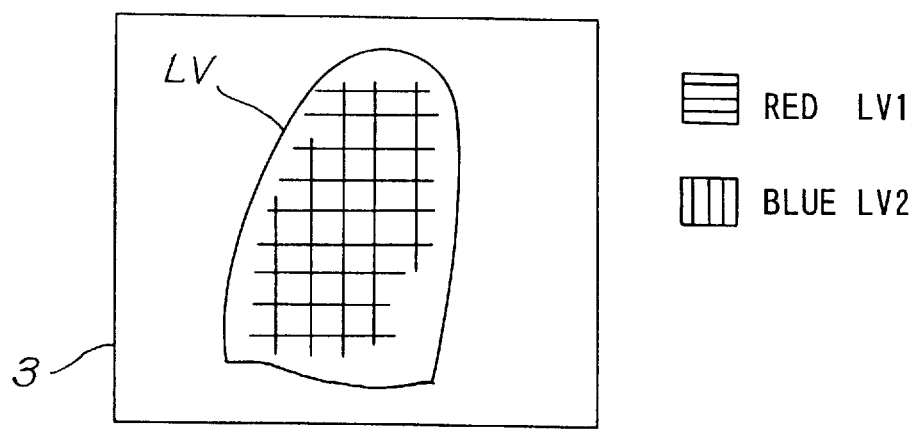
FIG. 17 is a conceptual view showing a transparent display example of a divided image of the left ventricle.

With respect to an image display method, for example, as shown in FIG. 16, the front-side and back-side left ventricles LV1 and LV2 divided into two sections on the division plane may be displayed simultaneously in parallel on the monitor 3; and as shown in FIG. 17, the front-side left ventricle LV1 may be transparently displayed in red or the like on the monitor 3; and the back-side left ventricle LV2 may be transparently displayed in blue or the like by changing the color. In this case, it becomes possible to visually perform diagnosis all over the left ventricle of the heart. In three-dimensional display of myocardial muscle perfusion, if no ischemia occurs, the entire left ventricles are indicated by purple; if ischemia occurs with the front-side left ventricle, it is indicated by blue; and if ischemia occurs with the back-side left ventricle, it is indicated by red.

When only one side of the left ventricles LV1 and LV2 divided into two sections is displayed, a position of the divided plane is moved so as to cover the entire left ventricles, making it possible to update the data any time. For example, as shown in FIG. 18, the division plane PL is preferably rotated around the long axis AX. In this manner, it becomes possible to diagnose the entire left ventricles of the heart. With respect to the above MIP display, as shown in FIG. 19A and FIG. 19B, an image may be mapped on a cardiac cavity boundary face S1 in a direction vertical to the boundary face S1; and the MIP target range may be restricted between the cardiac cavity boundary face S1 and a virtual exterior face S3 departed from its outside by a certain distance D3. In this case, there is an advantage that the meaning of an image is made clearer; an image can be generated using information on only the myocardial muscle site; and the calculation time is reduced more significantly. In particular, this effect becomes more significant during perfusion display using a contrast imaging method. In the case of integral value projection, similarly, surface rendering, or volume rendering other than MIP also, it is possible to restrictively project a region employed as data.

Figure 20A:
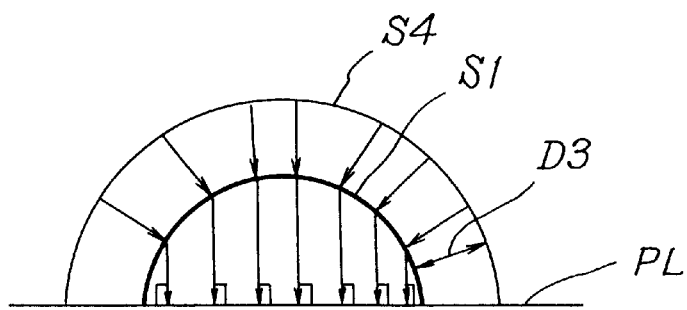
FIG. 20A is a conceptual view illustrating a projection example from the top of the cardiac cavity boundary face.
Figure 20B:
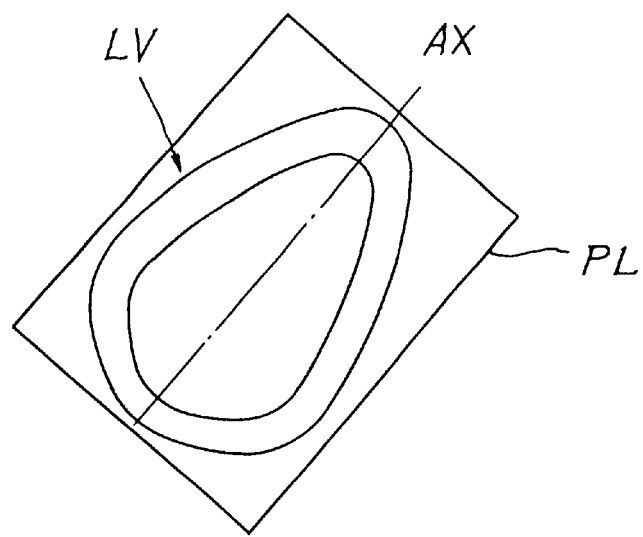
FIG. 20B is a conceptual view illustrating a setting example of a long axis of the left ventricle.

An image mapped on the above cardiac cavity boundary face S1, as shown in FIG. 20A can be mapped as a two-dimensional image on a predetermined division cross section PL by simple geometric projection. In this case, the division cross section PL can be manually set, referring to a three-dimensional image or can be automatically set as a plane passing through the long axis AX of the left ventricle LV as shown in FIG. 20B, respectively. In the latter case, the cross section can be detected as one of inertial main axes of the cardiac cavity or cardiac cavity boundary face or can be automatically detected using the other algorithm.

Figure 21A:
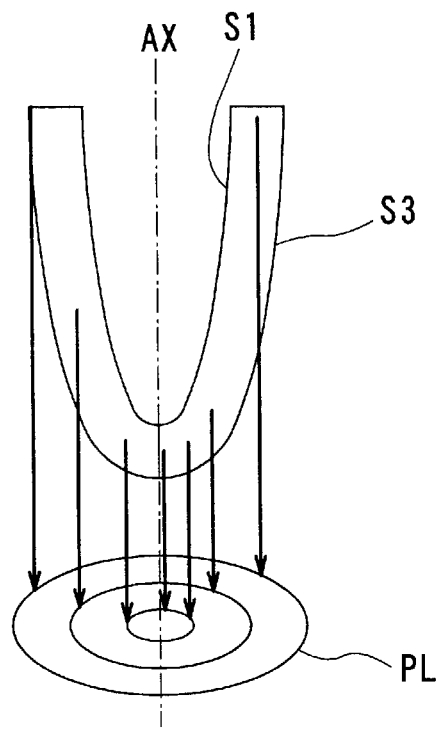
FIGS. 21A and 21B are a conceptual view illustrating another projection example obtaining a bull's-eye-like display image.
Figure 21B:
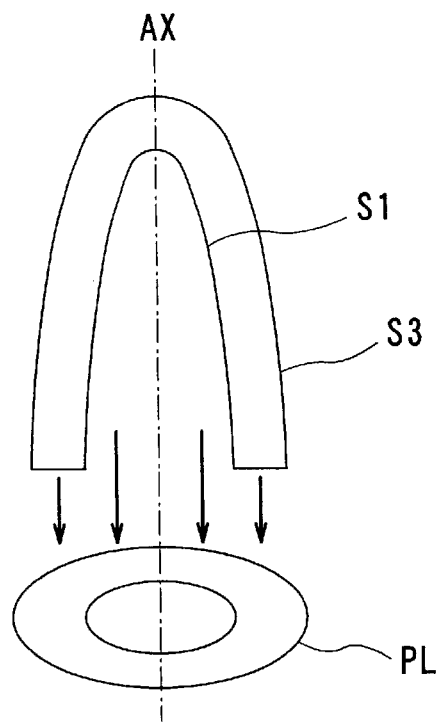

FIG. 21A and 21B show another imaging example. In this example, data between a cardiac cavity boundary face S1 and a virtual exterior face S3 departed from its outside by a certain distance D3 is projected on a predetermined projection plane PL according to a direction parallel to a long axis AX of a left ventricle by a projection processing such as MIP. As a result of such projection, a bull's-eye-like display image is obtained on the plane PL.

Processing functions such as the above mentioned cardiac cavity detection, masking of the blood flow image in the cardiac cavity, and coronary blood flow or perfusion display are preferably performed in real time with respect to a three-dimensional image acquired by a real-time three-dimensional ultrasonic diagnosis apparatus in order to help diagnosis. However, the above processing functions are, of course, applicable to a three-dimensional image reconstructed from a two-dimensional topographic image similarly without being limited thereto.

Therefore, although the above ultrasonic diagnosis apparatus is applied to a real-time three-dimensional system, the present invention is not always limited thereto, and is well applicable to a system capable of generating three-dimensional data.

Figure 22:
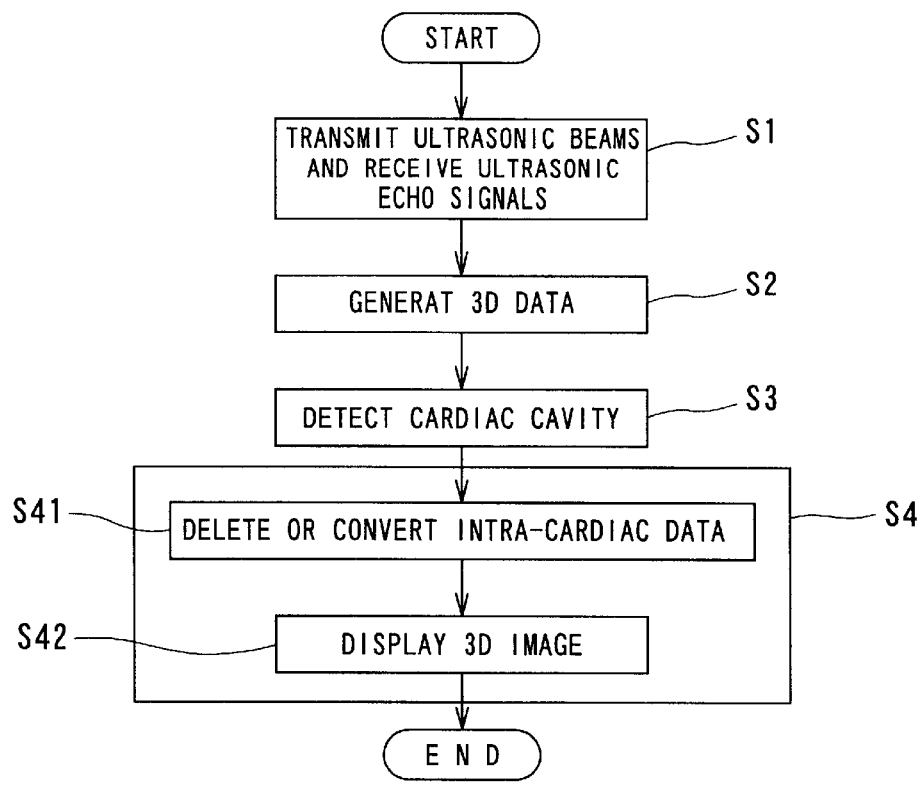
FIG. 22 is a schematic flowchart showing the procedural steps of the three-dimensional ultrasonic apparatus.
Figure 23:
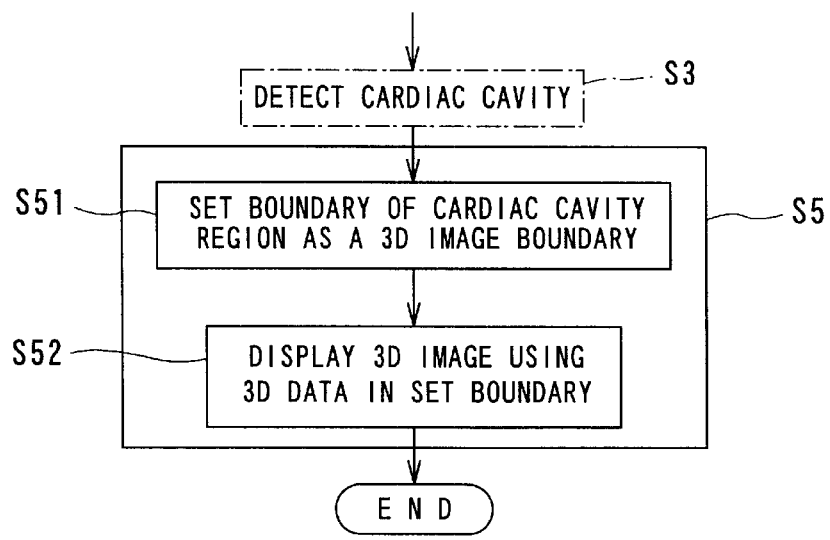
FIG. 23 is a schematic view showing the other procedural steps of the three-dimensional ultrasonic apparatus.

The schematic flowcharts shown in FIG. 22 and FIG. 23 summarize the procedural steps using the aforementioned three-dimensional ultrasonic apparatus. Hereinafter, the procedural steps will now be described.

As shown In FIG. 22, in step S1, the three-dimensional ultrasonic apparatus transmits ultrasonic beams to a diagnostic site including the left ventricle of the heart in the subject and receives its ultrasonic echo signals by transmitting and receiving means (including a 2D array probe and pulser/preamplifier unit in an example shown in FIG. 1).

Then, in step S2, three-dimensional data (three-dimensional morphological information, three-dimensional blood information such as velocity information and power value and contrast image with contrast imaging techniques using a contrast agent) concerning this diagnostic site from ultrasonic echo signals is generated by three-dimensional data generating means (including a receiving delay circuit, an echo processor, and a drive processor in an example shown in FIG. 1).

Next, in step 3, the aforementioned algorithm (for example, refer to FIG. 2 to FIG. 7 and descriptions thereof given previously) is executed by cardiac cavity detecting means (including a cardiac cavity detecting portion in an example shown in FIG. 1), and a cardiac cavity is detected from the three-dimensional data.

Then, in step S4, the aforementioned algorithm (for example, refer to FIG. 8 to FIG. 15 and descriptions thereof given previously) is executed from the three-dimensional data by display image generating means (including a 3D processor, a display unit, and a monitor); the intra-cardiac cavity data is deleted or converted (in step S41); a three-dimensional image in which the intra-cardiac cavity data has been deleted or converted is displayed on the monitor (step S42). (For example, refer to FIG. 16 to FIG. 21 and descriptions thereof given previously.)

In this case, as a specific example, there are assumed a case using MIP processing described below and volume rendering process.

(1) When MIP processing is employed

In this case, first, the three-dimensional image data in the cardiac cavity region is converted into a value indicating that there is a little or no blood flow (step S41), the three-dimensional image data after this conversion is MIPed along a projection direction, and is projected on a two-dimensional plane, thereby generating a display image (step S42).

(2) When volume rendering processing is employed

First, in this case, the three-dimensional image data in the cardiac cavity region is converted into a value with high transparency (step S41). Then, the three-dimensional image data after this conversion is subjected to volume rendering process along the projection direction, and is projected on the two-dimensional plane, and two-dimensional display image is generated (step S42). In volume rendering process, in general, the pixel transparency is set so as to be decreased according to an image value. Therefore, the value of the three-dimensional image data is converted into a value indicating that there is a little or no blood flow, thereby increase transparency. In addition, a method for increasing the setting of transparency provided corresponding to the position of three-dimensional data may be adopted.

(3) When another example of volume rendering process is employed

In this case, the three-dimensional image data in the cardiac cavity region is converted into data of color in which transparency is low, and color representative of blood flow can be easily identified (step S41). Then, the three-dimensional image data after this conversion is subjected to volume rendering process along a projection direction, and is projected on a two-dimensional plane, and the two-dimensional display image is generated (step S42). In this manner, a site with less myocardial blood flow is represented by a color assigned to the cardiac cavity region, and thus, the myocardial ischemia region can be easily identified.

In the procedural steps S1 to S4 shown in FIG. 22, it is possible to implement processing of step S4 singly or in parallel in place of the processing of step S5 shown in FIG. 23. That is, in this example, after each processing of steps S1 to S3 similar to that described previously, in step S5 a boundary of the cardiac cavity region is set as a boundary of a three-dimensional image by display image generating means (in step S51). A two-dimensional display image is generated from three-dimensional image data so that the data in the cardiac cavity region does not contribute to a display image based on the thus set cardiac cavity region boundary (step S52).

In this case, as a specific example, there is assumed a case when MIP processing and volume rendering process described below are employed.

That is, when MIP process is employed, MIP processing is done up to a cardiac cavity boundary region set along a direction across a myocardial muscle, and the thus obtained value is assigned to the cardiac cavity region boundary. Then, the value assigned to this cardiac cavity region boundary is projected on a two-dimensional plane, thereby generating a two-dimensional display image. In this manner, the data in the cardiac cavity region is limited in the image data processing range on the cardiac cavity region boundary so as not to be included in the image data processing range, thus making it possible to generate a two-dimensional display image from the three-dimensional image data so that the data in the cardiac cavity region does not contribute to the display image.

In addition, when volume rendering process is employed, three-dimensional data is projected on a two-dimensional plane along a projection direction, and a two-dimensional display image is generated. In this projection, the subject of volume rendering process is from the set cardiac cavity region boundary to a region on the myocardial side. The region on the myocardial side from the cardiac cavity region boundary is excluded from the subject of volume rendering process. In this manner, a two-dimensional display image can be generated from three-dimensional image data so that the data in the cardiac cavity region does not contribute to a display image.

What is claimed is:

1. A three-dimensional ultrasonic diagnosis apparatus comprising:
    a transmitter/receiver configured to transmit ultrasonic beams three-dimensionally to a diagnostic site including a left ventricle of a heart in a subject being examined and configured to receive ultrasonic echo signals thereof;
    a three-dimensional data generator configured to generate three-dimensional data of the diagnostic site based on the ultrasonic echo signals received by the transmitter/receiver;
    a cardiac cavity region determining mechanism configured to determine a cardiac cavity region in the three-dimensional data generated by the three-dimensional data generator, and
    a display image generator configured to generate a display image so as to display blood flow information in a myocardial site of the heart discriminated from blood flow information in the cardiac cavity region by converting a value of the cardiac cavity region to a different value.

2. The apparatus of claim 1, wherein the three-dimensional data generator is configured to generate at least one of morphological information of the diagnostic site, blood flow information of the diagnostic site, and the morphological information and the blood flow information as the three-dimensional data.

3. The apparatus of claim 2, wherein the cardiac cavity region determining mechanism is further configured to extract a cardiac endocardium from morphological inflation of the diagnostic site generated by the three-dimensional data generator to determine the cardiac cavity region based on the cardiac endocardium extracted.

4. The apparatus of claim 2, wherein the cardiac cavity region determining mechanism is further configured to obtain the cardiac cavity region based on the blood flow information of the diagnostic site generated by the three-dimensional data generator.

5. The apparatus of claim 2, wherein the transmitter/receiver is further configured to receive ultrasonic echo signals in a state of the subject into which a contrast agent is injected, the cardiac cavity region determining mechanism is further configured to determine the cardiac cavity region based on the three-dimensional data generated based on ultrasonic echo signals in the state of the subject by the three-dimensional data generator.

6. The apparatus of claim 1, wherein the display image generator is further configured to generate the display image based on data excluding the cardiac cavity region in the three-dimensional data.

7. The apparatus of claim 6, wherein the display image generator is configured to obtain two-dimensional image by projection of the three-dimensional data.

8. The apparatus of claim 7, wherein the display image generator is configured to obtain the two-dimensional image by using a predetermined projection method to project brightness information on data included in a region between a boundary face of the cardiac cavity in the three-dimensional data and a reference curved surface set from the boundary face with an arbitrary distance from the reference curved surface side.

9. The apparatus of claim 8, wherein the projection method includes a n MIP (Maximum or Minimum Intensity Projection) method.

10. The apparatus of claim 8, wherein the projection method includes an integral value projection method.

11. The apparatus of claim 7, wherein the two-dimensional image has a partial image of the three-dimensional data.

12. The apparatus of claim 11, wherein the partial image is a image included in a partial region of the left ventricle of the heart divided by a plane including a longer axis of the left ventricle.

13. The apparatus of claim 12, further comprising a detector configured to detect a long axis of the left ventricle of the heart based on the cardiac cavity determined by the cardiac cavity region determining mechanism.

14. The apparatus of claim 13, wherein the detector is further configured to detect one of a plurality of inertial main axes defined by morphology of the cardiac cavity as long axis on the left ventricle of the heart.

15. A three-dimensional ultrasonic diagnosis apparatus comprising:

a transmitter/receiver configured to transmit ultrasonic beams three-dimensionally to a diagnostic site including a left ventricle of the heart in a subject being examined and configured to receive ultrasonic echo signals thereof;

a three-dimensional data generator configured to generate three-dimensional blood flow information data of the diagnostic site based on the ultrasonic echo signals received by the transmitter/receiver;

a region determining mechanism configured to determine a cardiac cavity region in the blood flow information data generated by the three-dimensional data generator; and a display generator configured to generate a display image in which blood flow information in a cardiac cavity region is eliminated so as to display blood flow information in a myocardial site discriminated from blood flow information in the cardiac cavity region.

16. A three-dimensional ultrasonic diagnosis apparatus comprising:

a transmitter/receiver configured to transmit ultrasonic beams three-dimensionally to a diagnostic site including a left ventricle of a heart in a subject being examined and configured to receive ultrasonic echo signals thereof;

a three-dimensional data generator configured to generate three-dimensional blood flow information based on the ultrasonic echo signals received by the transmitter/receiver;

a display image generator configured to generate a display image so that a region with less blood flow information in a myocardial muscle of the heart is identified by changing an image processing method depending on a myocardial region and a cardiac cavity region of the heart so as to display blood flow information in a myocardial site discriminated from blood flow information in the cardiac cavity region; and a display configured to display the display image generated by the display image generator.

* * * * *